United States Patent [19]

Bennett

[11] Patent Number: Plant 6,141

[45] Date of Patent: Mar. 29, 1988

[54] MINIATURE ROSE PLANT NAMED 'DILLY DILLY'

[76] Inventor: Cecilia L. D. Bennett, 489 Minot Ave., Chula Vista, Calif. 92010

[21] Appl. No.: 825,791

[22] Filed: Feb. 3, 1986

[51] Int. Cl.[4] ..... A01H 5/00

[52] U.S. Cl. ..... Plt./9

[58] Field of Search ..... Plt./9

*Primary Examiner*—Robert E. Bagwill

[57] ABSTRACT

The subject of the present disclosure is a new and distinct variety of miniature rose plant, named 'Dilly Dilly', which is characterized by its blooms which range in color from near Rose Purple to near Magnolia Purple, usually borne one to a stem with hybrid tea form. The bush is vigorous, well-branched and produces moderate to heavy quantities of bloom.

1 Drawing Figure

The present invention relates to a new and distinct variety of a hardy, dwarf, bush plant of the miniature class; the variety being primarily characterized as a mauve.

The variety is further characterized by:

Long stemmed blooms of hybrid tea-type form, borne usually one to a stem but on occasion in sprays of 3 to 5 or more. The blooms are held very erect and well above the foliage.

It is very fragrant.

The plant ranges in height from 15 to 24 inches (40 to 60 cm). The canes are sturdy and erect with moderate branching and medium to heavy foliage covering. The plant is a moderate to heavy bloomer that does well either in the green house or outdoors.

The plant has a good growth habit, well-shaped and attractive, bearing numerous leaflets of average size.

The seed parent was Chrysler Imperial (U.S. Plant Pat. No. 1,528), and the pollen parent was a seedling of Plum Duffy (Miniature Rose Plant, mauve; Cecilia Bennett; introduced by Tiny Petals Nursery, 1978) and Magic Carrousel (U.S. Plant Pat. No. 3,601). It differs from its seed parent in the following ways. It is a miniature of the mauve classification, whereas Chrysler Imperial is a deep red hybrid tea. It differs from its pollen parents in the following ways. It is lighter shape of mauve than Plum Duffy, and Magic Carrousel is a red blend with no mauve tones.

The descriptive matter which follows, pertains to roses grown and color values observed in plants and newly opened blooms in the months of March through August 1985. The plants were grown outdoors in Chula Vista, Calif., and are believed to be accurate standards for this cultivar in similar conditions of soil and climate elsewhere.

The color photograph illustrates the variety.

Referring now specifically to the new and distinct variety of miniature rose plant named 'Dilly Dilly', the following is a detailed description thereof in outline; all major color plate identifications being by reference to the British Colour Council Horticultural Colour Chart, except where common terms of color definition are employed.

Type: Hardy, dwarf, bushy, green house or outdoor, decorative and exhibition potted plant.

Class: Miniature.

Variety name: Dilly Dilly.

Flowers borne: Usually one to a stem, but occasionally in sprays of 3 to 5 or more on erect stems with foliage well below the blooms.

Quantity of bloom: Moderate to heavy both outdoors or green house grown.

Bud:

*Peduncle.*—Variable in length (30 to 50 mm); average diameter and sturdy; ranging in color from near Lettuce Green (861 to 861/2 page 176) to near Scheeles Green (860 to 860/2 page 175) with some tinting of bronze.

*Hairs.*—Extremely small and sparse with a reddish color; located over the entire surface of the peduncle and sepals, but not present on the calyx tube.

*Calyx.*—Color ranging from near Lettuce Green (861 to 861/3 page 176) to near Scheeles Green (860 to 860/3 page 175).

*Opening.*—Opens well in all weather.

Bloom:

*Size when fully open.*—Average for a miniature variety (40 to 60 mm).

*Petalage.*—Full — averaging 25 to 35 petals, arranged regularly, plus petaloids (6 to 10 or more).

*Form.*—Urn-shaped to ovoid as the bloom progresses. The petals remain at first somewhat tightly cupped with the apex and/or margins reflexed outward, becoming at maturity more loosely cupped; and the petals reflexed more tightly (quilling), until each row of petals forms a five pointed star.

Petals: Fairly thick with good substance; both the upper and under surfaces of all petals have a matte finish.

*Shape.*—Outer petals are of a very broad obovate form. The intermediate petals are very much like the outer petals only narrower. The inner petals are a broad lanceolate form; and the petaloids are also lanceolate form with some occasional irregularities.

Color: Newly opened flowers from plants grown outdoors (March through August 1985), Chula Vista, Calif.

*All petals.*—Upper surface — Ranging from near Rose Purple (533/2 to 533/1 page 140) to near Magnolia Purple (030/3 to 030/2 page 114) with a tip of near Mimosa Yellow (602/3 to 602/1 page 143). Under Surface — Same as the upper surfaces.

*General color effect.*—Newly opened flowers are rich shades of near Rose Purple to near Magnolia Purple which fade only slightly in tone as the bloom matures, usually 5 to 7 days or more.

*Flower longevity.*—(March through August 1985) Plant in pot 4 to 7 days from bud with sepals reflexed to fully opened bloom. Holding at fully opened with gradual fading of color tones for 5 to 7 days or longer. Cut blooms at living room temperature 3 to 5 days or longer.

Reproductive organs:

*Stamens.*—A generous amount arranged uniformly around the pistil.

*Filaments.*—Varying in length with shorter filaments more proximal to the pistil; reddish in color with yellow anthers.

*Pollen.*—Abundant.

*Pistil.*—Short, abundant and spreading; reddish styles with pale yellow caps.

*Ovaries.*—All encased in calyx.

*Hips.*—Some.

*Seeds.*—One to five or more per hip.

*Sepals.*—Permanent; spear-shaped; open as the bloom opens, eventually recurves against the peduncle.

Foliage:

*Leaves.*—Five to seven leaflets on the average; medium size for a miniature rose plant.

*Leaflets.*—Broad ovate-shaped.

*Margin.*—Very serrated with occasional tinting of bronze, especially noticeable on the newer foliage.

*Color.*—Ranging from near Spinach Green (0960 to 0960/2 page 187) to near Scheeles Green (860 to 860/2 page 175) on the newer foliage with occasional bronzing of the margins, especially on the newer foliage. The upper surfaces have a semiglossy finish, and the under surfaces have a matte finish of a slightly lighter shade than the upper surfaces.

*Rachis.*—Medium strength; upper surface is grooved with very small hairs over the length of it. Under surface has few if any hairs but does contain 2 to 5 small thorns.

*Stipules.*—Varying in length from small to average width; tapering auricles angled outward at about 45 degrees.

Growth:

*Habit.*—Dwarf, bushy; large for a miniature rose plant.

*Growth.*—Vigorous and well-branched.

*Canes.*—Medium diameter; sturdy; held erect.

*Main stems.*—Color — Ranging from near Scheeles Green (860 to 860/2 page 175) to near Spinach Green (0960 to 0960/3 page 187).

*Thorns.*—Averaging 5 to 10 cm on the main stems and fewer on the branches. Reddish in color with occasional tinting of bronze. Small to average in size; slender and straight.

*Branches.*—Color — Same as the main stems.

The miniature rose plant and its flowers as herein described may vary in slight detail due to climate, soil and cultural conditions under which the variety may be grown; the present description being of the variety as grown in Chula Vista, Calif.

The following is claimed:

1. A new and distinct variety of miniature rose plant named 'Dilly Dilly' of a hardy, dwarf, moderate growth, well-branched and attractive appearance, substantially as illustrated and described, characterized by its blooms which range in color from near Rose Purple to near Magnolia Purple, easily asexually reproduced from cuttings, with flowers borne usually one to a stem, but occasionally in sprays of 3 to 5 or more.

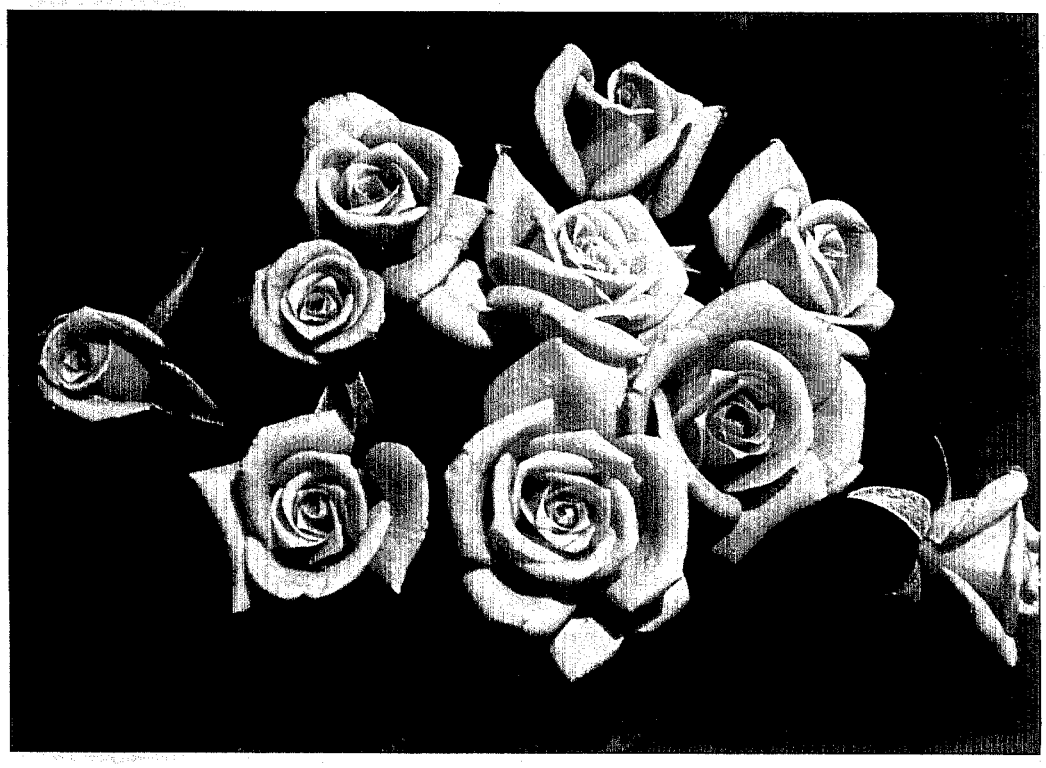

* * * * *